United States Patent
Calhoun

(10) Patent No.: US 9,961,946 B2
(45) Date of Patent: May 8, 2018

(54) MECHANISM FOR FOUNDATIONAL BREAST SUPPORT

(71) Applicant: Laura Calhoun, Elyria, OH (US)

(72) Inventor: Laura Calhoun, Elyria, OH (US)

(*) Notice: Subject to any disclaimer, the term of this patent is extended or adjusted under 35 U.S.C. 154(b) by 0 days. days.

(21) Appl. No.: 15/276,910

(22) Filed: Sep. 27, 2016

(65) Prior Publication Data

US 2018/0084841 A1   Mar. 29, 2018

(51) Int. Cl.
*A41C 3/14* (2006.01)

(52) U.S. Cl.
CPC .......... *A41C 3/144* (2013.01); *A41B 2400/52* (2013.01); *A41B 2400/60* (2013.01)

(58) Field of Classification Search
CPC ....... A41C 3/00; A41C 3/0021; A41C 3/0065; A41C 3/12; A41C 3/144; A41C 3/014; A41C 3/012; A41D 27/12; A41D 27/13; A61F 13/15; A61F 13/14; A41B 9/12
USPC .................................. 120/60, 37, 81, 54–57
See application file for complete search history.

(56) References Cited

U.S. PATENT DOCUMENTS

| | | | | |
|---|---|---|---|---|
| 4,295,469 A * | 10/1981 | Lindgren | ............... | A41C 3/142 450/56 |
| 4,992,074 A * | 2/1991 | Diaz | ...................... | A41C 3/065 2/267 |
| 5,603,653 A * | 2/1997 | Hartman | .................. | A41B 9/12 2/267 |
| 5,980,359 A * | 11/1999 | Brown | ...................... | A41C 3/12 450/14 |
| 6,074,272 A * | 6/2000 | Hebert | .................. | A61F 13/141 450/37 |
| 6,264,530 B1 * | 7/2001 | Cosentino | ................ | A41C 3/12 2/267 |
| 6,341,377 B1 * | 1/2002 | Faries, Jr. | .............. | A41D 27/13 2/53 |
| 7,001,241 B2 * | 2/2006 | Gorringe | ............... | A61F 13/141 450/37 |
| 7,404,752 B1 * | 7/2008 | Karon | ...................... | A41C 3/12 2/53 |
| 7,416,544 B2 * | 8/2008 | Sakaguchi | ............ | A61F 13/141 450/37 |
| 7,607,966 B1 * | 10/2009 | Fox | ....................... | A41C 3/0021 450/55 |
| 7,905,763 B1 * | 3/2011 | Frank | ...................... | A41D 27/12 450/37 |
| 9,005,177 B2 * | 4/2015 | Krasikoff | ................ | A61F 13/45 604/385.01 |
| 2008/0004588 A1 * | 1/2008 | Gavitt | ...................... | A41C 3/00 604/385.07 |
| 2010/0069869 A1 * | 3/2010 | Johnston | ............... | A61F 13/141 604/385.02 |
| 2014/0302745 A1 * | 10/2014 | Golubovic | .............. | A61F 13/15 450/1 |
| 2017/0000194 A1 * | 1/2017 | Huyghe | ............... | A41C 3/0035 |

* cited by examiner

*Primary Examiner* — Gloria Hale
(74) *Attorney, Agent, or Firm* — Kathryn A. Perales

(57) ABSTRACT

Existing brassieres fail to provide adequate comfort and lift to many women with breasts of size C cup and larger. The invention is a cushiony pad which is attached via a flap to the inside of a brassiere cup. When donning the brassiere, the woman inserts the pad into the inframammary fold, between the underside of the breast and the chest. The pad acts as a platform for the breast, allowing the breast to rest on top of it, lifting the breast up and providing comfort and support.

4 Claims, 4 Drawing Sheets

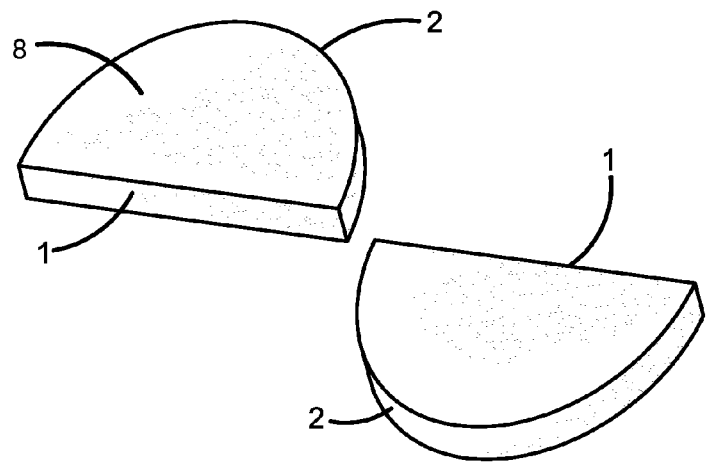
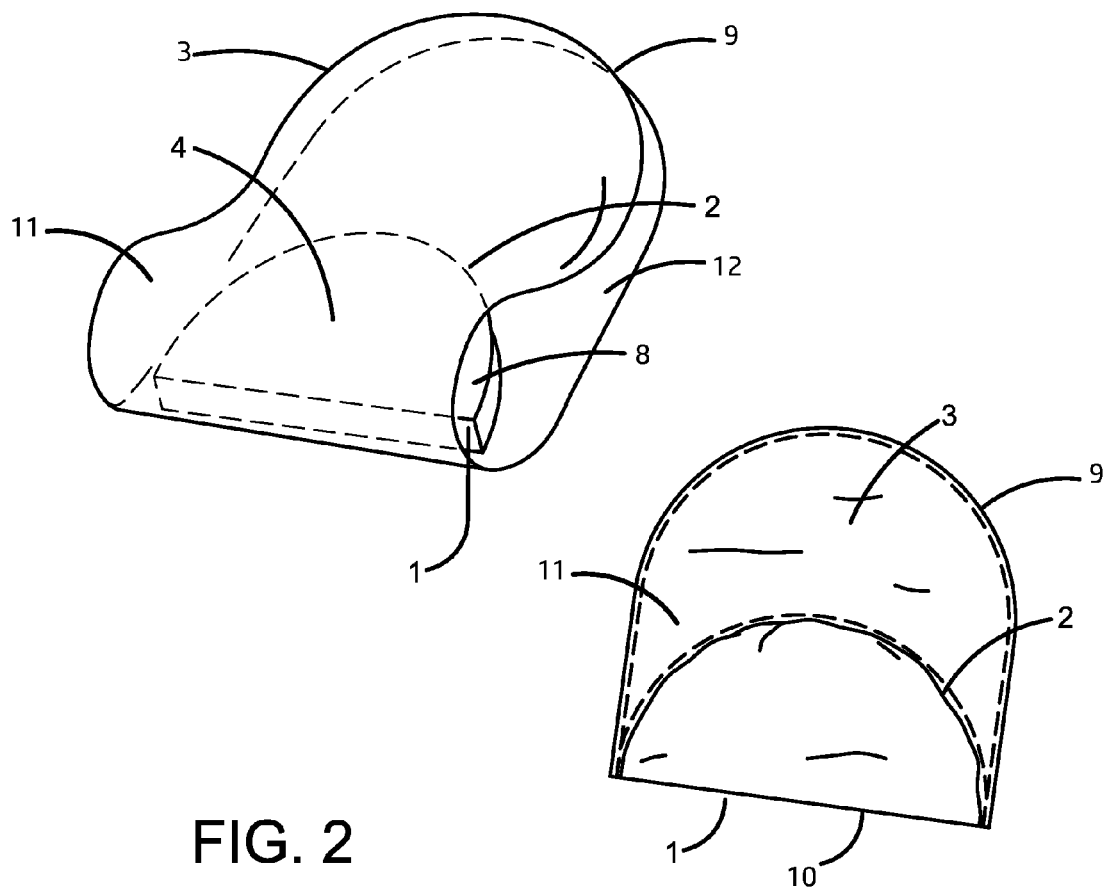
FIG. 1
FIG. 2

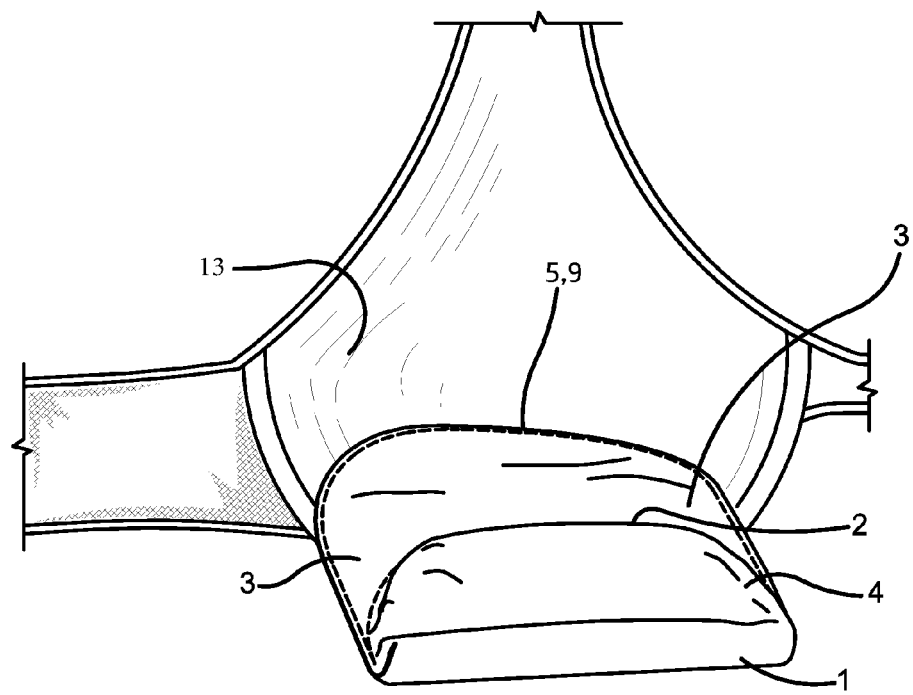
FIG. 4
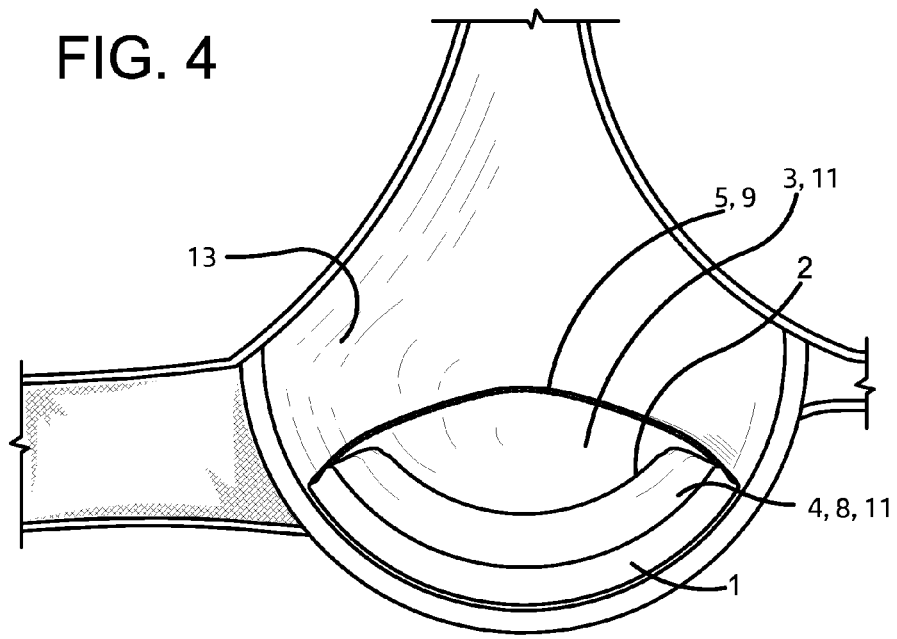

MECHANISM FOR FOUNDATIONAL BREAST SUPPORT

BACKGROUND OF THE INVENTION

Field of the Invention

The present invention relates to brassieres incorporating under breast support for breasts that are a C cup or larger.

Description of the Related Art

In women who have breasts of a C cup size or larger, the unsupported shape of the breasts is often not the firm, solid shape that is expected in advertising media or popular culture. Existing bras pack and compress the breast into a cup which is the expected and commonly considered proper and attractive shape of a breast. When breasts are a C cup or larger, often some ptosis or sagging of the breast exists, and the skin is rarely tight enough to cause the bottom surface of the breasts to protrude horizontally; instead, the weight and bulk of the breast falls below the inframammary fold, which is the imaginary line on the skin where the chest meets the bottom of the breast, and some portion of the skin on the underside of the breast touches the skin on the chest, under the breast.

In existing brassieres made for A and B cup sizes, the lower bands and/or underwires are intended to, and usually do, contact the woman's skin at or near the inframammary fold. However, existing brassieres made for C cup sizes and larger often do not contact the woman's skin at the inframammary fold; instead the lower bands and/or underwires rest in a line on the skin of the chest below the inframammary fold, such that the skin on the underside of the breast is in contact with the skin of the chest. Existing brassieres made for C cup sizes and larger often compress the breast in such a way as to press some portion of the skin on the underside of the breast against the skin on the chest, under the breast. The skin on skin contact can cause sweating, chafing, a rash such as intertrigo, and general discomfort.

Breasts of a C cup or larger size are heavier, and more likely to sag and stretch (ptosis) than smaller breasts. Sometimes the breasts have excess skin due to weight loss. Women with breasts of a C cup or larger sometimes experience back pain and shoulder pain due to existing brassieres which support the breasts mainly from the shoulder straps. Some existing brassieres claim to support the breasts from underneath with partially rigid foam cups and/or underwires, but the weight of the breasts is truly supported in the end by the shoulder straps.

Many women with breasts of C cup and larger are unable to find comfortable brassieres. Underwires often land in a spot which causes pain; sports bras often uncomfortably crush the breasts; thin or badly placed shoulder straps can cut into the shoulder as a result of supporting too much weight; tightly fitting cups and lower bands can cause part of the breasts to spill out of the sides or top of the cups; and shoulder straps tightened to attempt to lift the breasts sometimes backfire, causing the breasts to spill out of the bottom of the bra, under the lower band.

Going without a brassiere is usually not a viable option for women, for reasons of modesty; discomfort when moving around without support; chafing of the underside of the breast rubbing against the skin of the chest; and feelings that unsupported breasts with ptosis are not attractive. The inventor has found that the most desired feature of a brassiere is to combat sagging and lift up the breasts. Another highly desired feature is for the brassiere to fit in such a way that the wearer does not notice the brassiere while wearing it—noticing the brassiere normally means that it is uncomfortable or unsupportive in some way.

BRIEF SUMMARY OF THE INVENTION

The invention is a shaped cushiony pad which is connected on one end via a flap to the inner side of a cup of a brassiere, and which is inserted into the area between the underside of the breast and the chest, all the way up to and touching the inframammary fold. The pad, which may be made of some type of foam or other comfortable, cushiony material, and which may be covered with fabric or other material, prevents the skin on the underside of the breast from touching and rubbing against the skin of the chest. Simply by being wedged into the space between the underside of the breast and the chest, the pad provides support and lift to the breast from underneath, alleviating tension and weight which normally pulls on the shoulder straps of the brassiere.

BRIEF DESCRIPTION OF THE SEVERAL VIEWS OF THE DRAWINGS

FIG. 1 shows two oblique views of the pad.

FIG. 2 shows an oblique view of the pad shown in FIG. 1, with a flap in place but not yet attached to the pad. FIG. 2 also shows a view of the pad encased in the flap.

FIG. 4 shows two versions of the same partial view of the inner side of a brassiere, with the flap and pad attached. The upper view shows the flap and pad extended, and the lower view shows the flap and pad in place in the brassiere cup.

DETAILED DESCRIPTION OF THE INVENTION

The invention is a pad which is attached to a brassiere, and which is tucked into the space between the underside of the breast and the chest below the breast. The pad has a straight end which tucks horizontally into the inframammary fold, and an arc-shaped or curved end which is attached via a cloth-like extension or flap to the inside of the cup of the brassiere. A brassiere is herein defined to mean a garment which is intended to receive, support and cover some portion of the breasts. A cup of a brassiere is herein defined to mean the area of a brassiere which is designed to receive a breast—it may not have a defined cup or breast shape, as in some sports bras.

FIG. 1 shows the approximate shape of the pad. The embodiment of the pad shown is approximately the same thickness throughout. The straight end 1 will be tucked into the inframammary fold, and the curved end 2 will protrude forwards and roughly mimic the curvature of the front of the breast and brassiere cup. The pad has a top side 8, and a bottom side located opposite the top side. The pad may be cut to the desired size and shape from a piece of foam or other cushiony material, or it may be molded, shaved, trimmed or formed in some other way. The pad may be formed by attaching multiple layers of cushiony material together. It may also be formed by creating an empty envelope of appropriate shape and size, which is then filled with cushiony material, like a pillow or bean bag.

Figure 3:
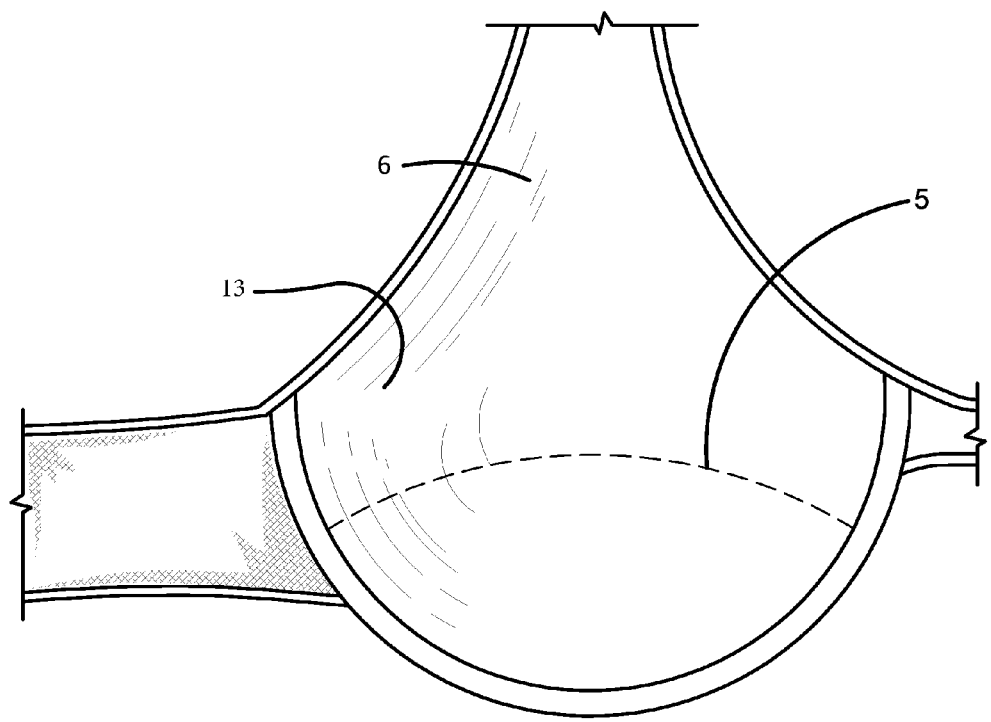
FIG. 3 shows a partial view of the inner side of a brassiere, and shows the line where the flap shown in FIG. 2 would be attached.

FIG. 2 illustrates the shape and placement of the flap 3, which flap 3 is attached to the pad 4 by folding the flap 3 in half as shown, and placing the pad 4 inside of the flap 3 such that the straight end of the pad 1 touches the inner side of the straight end of the flap 10. The flap 3 has a top outside surface 11 and a bottom outside surface, neither of which touch the pad 4. The flap's top inside surface touches the pad's top side 8, and the flap's bottom inside surface 12 touches the pad's bottom side. The pad 4 is snugly encased within the folded flap 3 by sewing through or otherwise attaching both layers of the flap around the pad's curved end 2. The flap 3 also has a curved end 9, such that it can be sewn or otherwise attached into the inside concave surface 13 of the brassiere cup, along the line 5, as shown in FIGS. 3 and 4. The exact shape and curvature of the curved end of the flap 9 will match the shape and curvature of the inside concave surface 13 of the brassiere cup to which it is to be attached.

FIG. 3 shows a partial view of a brassiere, including one of the cups 6, which is viewed as if the cup 6 were protruding into the paper, away from the viewer. The inside concave surface 13 of the brassiere cup is shown rather than the cup's outside convex surface. The dashed line 5 represents the approximate area where the flap 3 will be sewn or otherwise attached to the cup 6.

FIG. 4 shows the same partial view of a brassiere shown in FIG. 3, with the curved end of the flap 9 attached to the cup 6 along the line 5, and the flap 3 and pad 4 shown as if protruding out of the paper, towards the viewer. FIG. 4 also shows the same partial view of a brassiere, with the curved end of the flap 9 attached to the cup 6 along the line 5, and the flap 3 and pad 4 shown in place in the brassiere cup 6 as they would rest when the brassiere is being worn.

Figure 5:
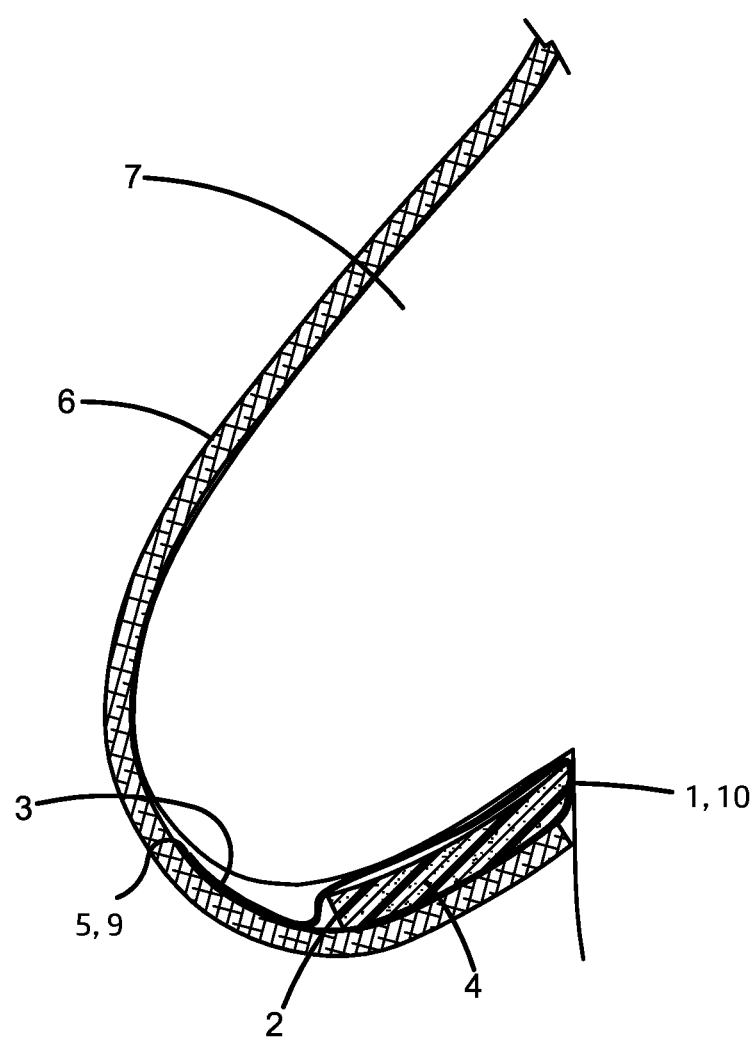
FIG. 5 shows a cutaway view, from the side, of a breast in a brassiere cup with the pad tucked under the breast and attached to the inside of the cup of the brassiere.

FIG. 5 shows a cutaway view, from the side, of a woman's breast 7 encased in a brassiere cup 6 with the pad 4 and flap 3 installed and being used. The curved end of the flap is shown sewn into the brassiere cup 6 at the line 5, and the straight end of the pad 1 is shown to be in the same location as the straight end of the flap 10.

In one embodiment, for use in with cups from size D to DDD, the pad is made of 1 inch (2.5 cm) thick polyurethane foam. The straight end of the pad in this embodiment is 6.5 inches (16.5 cm) long, and the distance from the midpoint of the straight end to the midpoint of the curved end is 2.5 inches (6.3 cm). In another embodiment for a brassiere with cups of the same size, from D to DDD, the pad is 2 inches (5.1 cm) thick, 7 inches (17.8 cm) long and 3 inches (7.6 cm) from the midpoint of the straight end to the midpoint of the curved end. The size, shape and thickness of the pad and flap will vary according to the size, weight, and degree of sagging/ptosis of the breasts of the woman for whom the foundational breast support is intended.

The inventor believes that many types of cushiony material for the pad would work well, including but not limited to foam rubber; polyurethane; high density foam; non-allergenic foam; latex rubber foam; Evlon or Lux; high resilience foam; Supreem foam; Rebond foam; closed cell foam, which would not absorb water; Dryfast foam; low density foam; open cell foam; laminate foam; stretch spacer foam; polylaminate foam; polyester foam; memory foam; cotton stuffing; polyester stuffing; Poly-Fil foam; feathers, either real or synthetic; cotton batting; polyester batting; wool batting; bamboo batting; bonded batting; fusible batting; needle punch batting; cluster fiber; polyester/cotton stuffing; synthetic down; recycled, "green" or eco-friendly materials; hypoallergenic materials; microbeads; polyester pellets; polystyrene beads; tricot-bonded poly filler; sterile, latex free, antibacterial gauze; and cellulose and super absorbent polymere powder layers. The pad may contain one or more layers of the same or different materials.

In one embodiment, the pad is covered with fabric and has a fabric flap which extends from the curved end. The fabric flap is sewn or otherwise attached onto the inside of the brassiere cup, along a line which is horizontal and approximately centered vertically in the cup. The fabric used to cover the pad and/or attach the pad to the brassiere cup can be any type of fabric. The inventor has found cotton/polyester blend to be comfortable and work well. In an embodiment for use with cups from size D to DDD, the fabric flap extends out 3 inches (7.6 cm) from the middle of the curved end of the pad.

In one embodiment, the covering and flap are made of one piece of fabric which encases the pad and extends from the curved end of the pad to the inside of the brassiere cup.

The inventor believes that many types of fabric coverings for the pad would work well, including but not limited to cotton/polyester blends of different ratios; cotton/polyester/spandex blends; cotton; Lycra; Lycra/spandex blends; cotton jersey knit; cotton spandex knit; modal knit; polyester tricot; nylon/spandex blends; nylon; Techsheen; contoured fabric; microfiber; one-way stretch fabric; two-way stretch fabric; nylon tricot; bamboo rayon; and Dri FIT fabric. The fabric covering for the pad may or may not be the same material as the flap.

In the embodiment shown in FIGS. 3 and 4, the flap is attached to the inside of the brassiere cup along an approximately horizontal and vertically centered line. This placement has been found to work well with cup sizes from D to DDD. For these and other sizes and shapes of breasts, the optimal line of attachment may well be vertically farther up or down in the cup.

The pad acts as a platform for the breast, allowing the breast to rest on top of it, lifting the breast up from underneath and providing support and comfort. See FIG. 5. Use of the invention reduces jiggling, bouncing and general movement of the breast, partly because the breast fits more appropriately in the brassiere cup with the pad in place. Strain on the back and shoulders, normally caused by the shoulder straps supporting all of the weight of the breast, is largely alleviated. The need to constantly adjust the brassiere's straps and band is eliminated or greatly reduced, which achieves the desired features of lift, support and a brassiere fit that the wearer does not notice because of its comfort—a great improvement over the existing art.

While the pad supports much of the weight of the breast and reduces some of the strain on the shoulder straps, the shoulder straps still carry some of the weight of the breasts. In a preferred embodiment, the shoulder straps are thick, at least one inch wide, and have a layer of foam 6¼ inches long, ¼ to 1 inch thick and ¼ inch wide incorporated inside the part of the strap which contacts the top of the shoulders. Foam can similarly be added for comfort to the bottom band of the brassiere, which encircles the torso under the breasts.

The invention works most conveniently with brassieres that have closures in the front, but also works with brassieres that have closures in the back, and also brassieres that have no closures, such as sports bras. The invention works with many types of brassieres, including but not limited to underwire, full cup and sports bras.

Although the invention is envisioned to provide much benefit for those with breasts of C cup size and larger, there may be situations where those with smaller breasts will also benefit, especially where ptosis is present and/or when a normal brassiere causes skin on skin contact at the inframammary fold.

To combat excessive perspiration; the pad may incorporate foam and sterile, latex free, antibacterial gauze; or foam surrounded by absorbent materials that normally make up sanitary napkins, such as cellulose and super absorbent polymere powder layers. These pads would be disposable, and so they would be easily attachable to and detachable from the brassiere. Such disposable pads may fasten to or into a flap, which would be permanently attached to the cup of the brassiere; alternatively, a disposable pad and flap combination may be used and replaced.

The invention claimed is:

1. An assembly for supporting a human breast, said assembly comprised of:
   (a) A pad, made of foam or other material that would be comfortable and like a cushion, of approximately semicircular shape, with a thickness, a straight end and a curved end, each of which has a midpoint and said ends are located opposite each other, a width having a length measurement of the straight end, a length having a length measurement between the midpoints of the straight end and the opposite curved end, a top side, and a bottom side; and
   (b) a flap, made of one piece of fabric which is then folded into two layers, with a width slightly greater than the width of the pad, which flap, when folded to form a fold, has a folded length, a top outside surface, a bottom outside surface, a top inside surface, a bottom inside surface, a first curved end with double layers, and a second straight end located at the fold; and
   (c) a brassiere cup with an inside concave surface and an outside convex surface;
wherein the pad is placed inside the folded flap, with the top side of the pad touching the top inside surface of the flap, and with the bottom side of the pad touching the bottom inside surface of the flap, and with the straight end of the pad touching the inside of the fold at the second straight end of the flap; and
wherein the pad is snugly encased inside of the folded flap by sewing through or otherwise attaching both layers of the flap around the curved end of the pad, thus preventing the pad from moving around inside of the flap and also preventing the pad from coming out of the flap; and
wherein the flap's first curved end is sewn or otherwise attached into the inside concave surface of the brassiere cup along a horizontal line across the brassiere cup.

2. The breast support assembly of claim 1, wherein the assembly is a permanent part of a conventional brassiere.

3. A method of supporting breasts, comprising the steps of:
   (a) providing a pad, configured to be inserted into an area between an underside of a breast and a chest, up to and touching an inframammary fold, which pad is made of foam or other material that would be comfortable and like a cushion, of approximately semicircular shape, with a straight end and a curved end, each of which has a midpoint and said ends are located opposite each other, a width having a length measurement of the straight end, a length having a length measurement between the midpoints of the straight end and the opposite curved end; a top side; and a bottom side, and which pad is permanently attached to the inside of a brassiere cup via a fabric flap, which brassiere cup is part of a brassiere;
   (b) manually lifting the breast and inserting the straight end of the pad horizontally into the area between the underside of the breast and the chest, up to and touching the inframammary fold, while the unfastened brassiere remains attached to the flap and pad; and
   (c) continuing to don the brassiere;
wherein the brassiere cup has an inside concave surface; and
wherein the-pad is encased inside of the fabric flap, which is made of one piece of fabric which is then folded into two layers, with a width slightly greater than the width of the pad, which flap, when folded, has a first curved end with double layers, and a second end located at the fold, and which folded flap encases the pad by being sewn through both layers of the flap around the curved end of the pad, and which flap's first curved end is sewn or otherwise attached into the inside concave surface of the brassiere cup along a horizontal line across the brassiere cup; and
wherein the pad supports and lifts the breast from underneath, allowing the breast to rest on top of the pad.

4. An assembly for supporting a breast, said assembly being comprised of:
   (a) a pad, made of foam or other material that would be comfortable and like a cushion, of approximately semicircular shape with a uniform thickness, a straight bottom end with a midpoint, a curved top opposite end with a midpoint, a width having a length measurement of the straight bottom end, a length having a length measurement between the midpoints of the straight bottom end and of the curved top opposite end, and a top side and a bottom side; and
   (b) a flap, made of one piece of fabric with a length, folded over into two layers lengthwise creating a fold, with a width slightly greater than the width of the pad, which flap has a top outside surface, a bottom outside surface, two inside surfaces, two straight sides, a first curved end and a second opposite end at the aforementioned fold; and
   (c) a brassiere cup of a brassiere, with an inside concave surface and an outside convex surface;
wherein the pad is encased inside the folded flap, touching both inside surfaces of the flap and wherein the straight bottom end of the pad aligns horizontally at the flap's second opposite end at the aforementioned fold, wherein the curved top opposite end of the pad and the first curved end of the flap are parallel; and
wherein the pad and flap can be sewn or otherwise attached together to form a one piece assembly, by sewing or otherwise attaching through both the top outside surface and the bottom outside surface of the flap around the curved top end of the pad, excluding the folded end where the pad and flap are aligned, which prevents the pad from moving around inside the flap, and also sewing or otherwise attaching through both the top outside surface and the bottom outside surface of the flap around the two straight sides and the first curved end of the flap, excluding the folded end where the pad and flap are aligned; and
wherein the flap's first curved end of the one piece assembly is sewn or otherwise attached into the inside concave surface of the brassiere cup along a horizontal line across the brassiere cup; and
wherein the assembly is one piece made up of a pad and a flap which are permanently attached to the interior of a brassiere cup making it one with a brassiere, and which assembly is configured to provide foundational breast support by lifting the breast up from underneath when the assembly is placed horizontally underneath the breast into the inframammary fold where the breast and chest wall meet, and the weight of the breast rests fully on the assembly instead of resting against the chest wall, thus eliminating skin to skin contact, and when the breast is lifted up from the bottom, the breast is better supported and better fills the brassiere cup.

* * * * *